United States Patent
Valkanas et al.

(10) Patent No.: US 6,168,642 B1
(45) Date of Patent: Jan. 2, 2001

(54) INDUSTRIAL UTILIZATION OF GARBAGE WITH EFFECTIVE RECYCLING AND WITH OPTIMIZATION IN ENERGY PRODUCTION

(75) Inventors: George Valkanas, Maroussi; Apostolos G. Vlyssides, Attica, both of (GR)

(73) Assignee: Innoval Management Limited (AN)

( * ) Notice: Under 35 U.S.C. 154(b), the term of this patent shall be extended for 0 days.

(21) Appl. No.: 09/101,015

(22) PCT Filed: Dec. 17, 1996

(86) PCT No.: PCT/GR96/00025

§ 371 Date: Nov. 24, 1998

§ 102(e) Date: Nov. 24, 1998

(87) PCT Pub. No.: WO97/24186

PCT Pub. Date: Jul. 10, 1997

(30) Foreign Application Priority Data

Dec. 29, 1995 (GR) .............................. 950100473

(51) Int. Cl.[7] .............. C05F 9/00; C05F 11/08; D21B 1/08; D21C 11/00; D21C 11/06; B02C 17/00; B02C 17/02; B03B 5/64; C02F 3/30; C02F 3/00; C02F 3/02

(52) U.S. Cl. .............. 71/9; 71/10; 71/14; 162/4; 162/14; 162/15; 209/162; 209/930; 210/605; 210/612; 210/613; 210/620; 210/621; 210/623; 241/20; 241/24.1; 241/24.12; 241/24.13; 241/24.14; 241/24.18; 241/24.2; 241/24.22; 241/24.9

(58) Field of Search ............... 71/9, 10, 14; 423/DIG. 3; 209/162, 930; 241/20, 24.1, 24.12, 24.13, 24.14, 24.19, 24.2, 24.18, 24.22; 210/605, 612, 613, 620, 621, 623, 928; 162/4, 14, 15

(56) References Cited

U.S. PATENT DOCUMENTS

| | | | |
|---|---|---|---|
| 3,817,458 | * 6/1974 | Gilberto | 241/20 |
| 3,933,577 | 1/1976 | Penque | 162/4 |
| 4,157,961 | 6/1979 | Borst | 210/33 |
| 4,185,680 | 1/1980 | Lawson | 162/5 |
| 4,632,692 | * 12/1986 | Lebesgue et al. | 71/10 |
| 4,959,123 | * 9/1990 | Lehmann et al. | 162/5 |

FOREIGN PATENT DOCUMENTS

| | | |
|---|---|---|
| 3531605A1 | 5/1987 | (DE) . |
| 0474895A1 | 9/1990 | (EP) . |
| 0286100B1 | 10/1991 | (EP) . |
| 0521685A2 | 6/1992 | (EP) . |
| 1001916 | 6/1994 | (GR) . |
| 1002265 | 3/1995 | (GR) . |

* cited by examiner

Primary Examiner—Wayne Langel
Assistant Examiner—Maribel Medina
(74) Attorney, Agent, or Firm—Birch, Stewart, Kolasch & Birch, LLP

(57) ABSTRACT

A recycling process for garbage containing a high proportion of paper where printed paper is first separated from the garbage. The garbage is then into pieces and light and heavy components are separated out in a classification tank. The remaining organic mass suspended in water is hydrolyzed and subjected to anaerobic digestion followed by aerobic co-composting. The resulting solid is a high grade fertilizer while biogas produced by the process is converted to electrical energy in a combined cycle installation.

19 Claims, 3 Drawing Sheets

FLOATING UNIT SECTION VIEW top view cross section

FLOATING UNIT SECTION VIEW

INDUSTRIAL UTILIZATION OF GARBAGE WITH EFFECTIVE RECYCLING AND WITH OPTIMIZATION IN ENERGY PRODUCTION

This application is the national phase under 35 U.S.C. §371 of prior PCT International Application No., PCT/GR96/00025, which has an International filing date of Dec. 17, 1996, which designated the United States of America, the entire contents of which are hereby incorporated by reference.

FIELD OF THE INVENTION

The present invention relates to a method for recycling garbage by separating paper following by anaerobic digestion.

BACKGROUND OF THE INVENTION

We have invented and proved widely in practice a unit of anaerobic digestion working with high stability in the thermophilic region described in our patent EP. 0474895.

We have additionally invented and proved in practice the treatment of sludge resulting after anaerobic digestion in aerobic composting in the thermophilic region with production of mixed humic-chemical-organic fertilizers of high purity and fertilizing value which are described in our patent GR. 1001916.

We have also invented and developed knowledge in the production of pulp and paper which is described in our patent GR (appln.) 950100110 and we have introduced it in our solution for garbage, where paper makes a main constituent. This is the separation of paper and treatment by de-inking and with mild chemical pulping for the production of pulp of high value.

The garbage after the separation of 75–80% of paper has the composition:

| | |
|---|---|
| Paper | 14–17% |
| Food wastes | 40–50% |
| Garden wastes | 8–10% |
| Polymers | 10–12% |
| Metals | 7–9% |
| Glass | 7–9% |

A complicated process for the treatment of solid waste producing fiber pulp and fertilizer is described in U.S. Pat. No. 3,933,577. However the present invention takes into consideration additional elements in such a way that our process has been developed for complete utilization of garbage with effective recycling and with using the remaining materials for energy production by anaerobic digestion in the thermophilic region most profitably.

DETAILED DESCRIPTION

Figure 1:
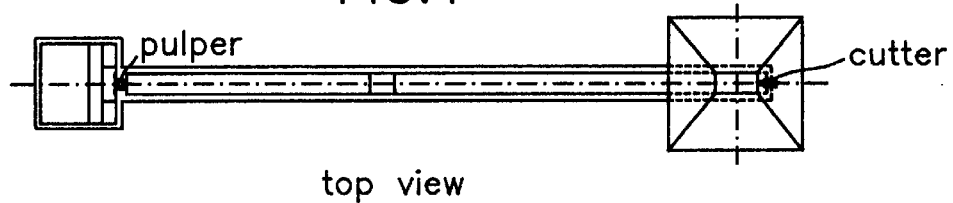
FIG. 1 is a top view of the floatation unit.
Figure 2:
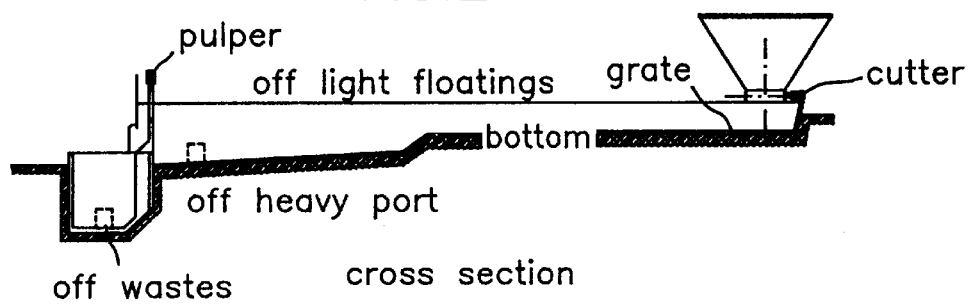
FIG. 2 is a cross sectional view of the floatation unit.
Figure 3:
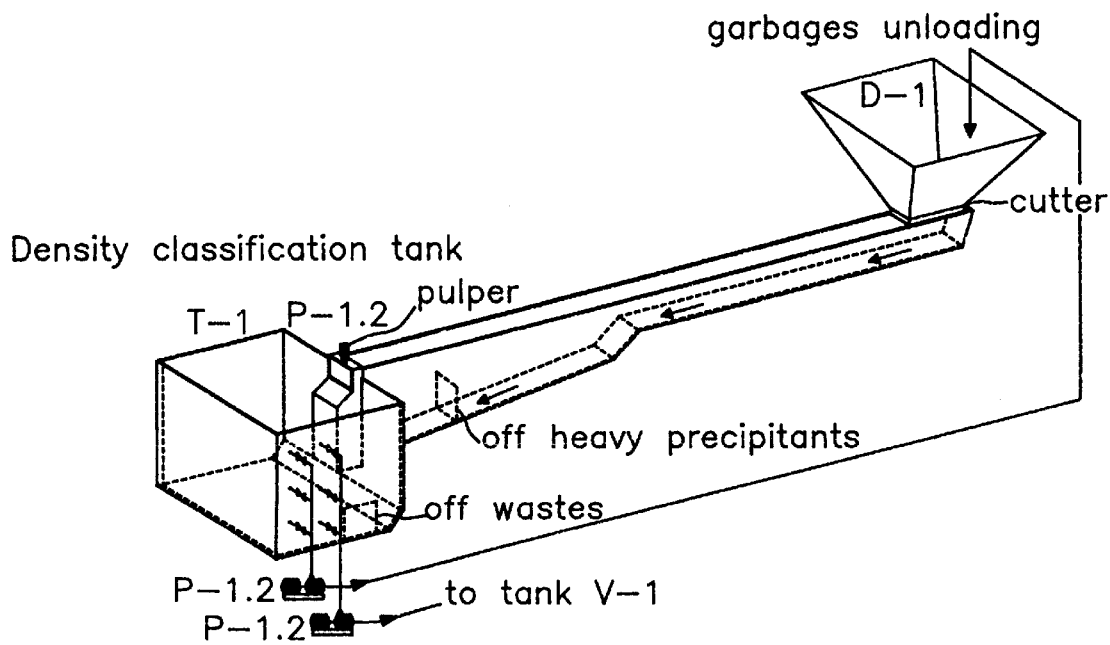
FIG. 3 is a section view of the floatation unit.
Figure 4:
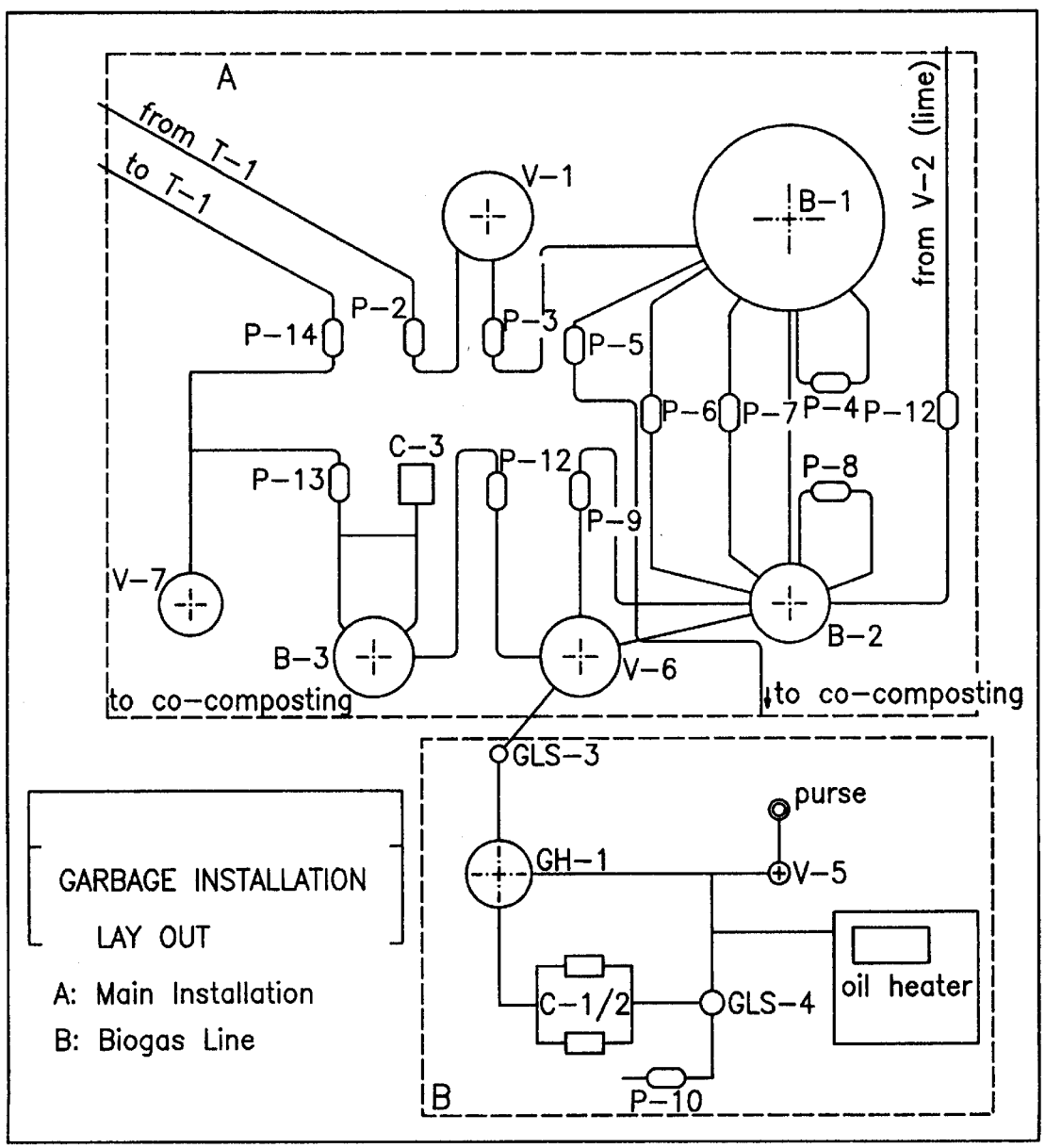
FIG. 4 is a diagram of the fertilizer plant.
Figure 5:
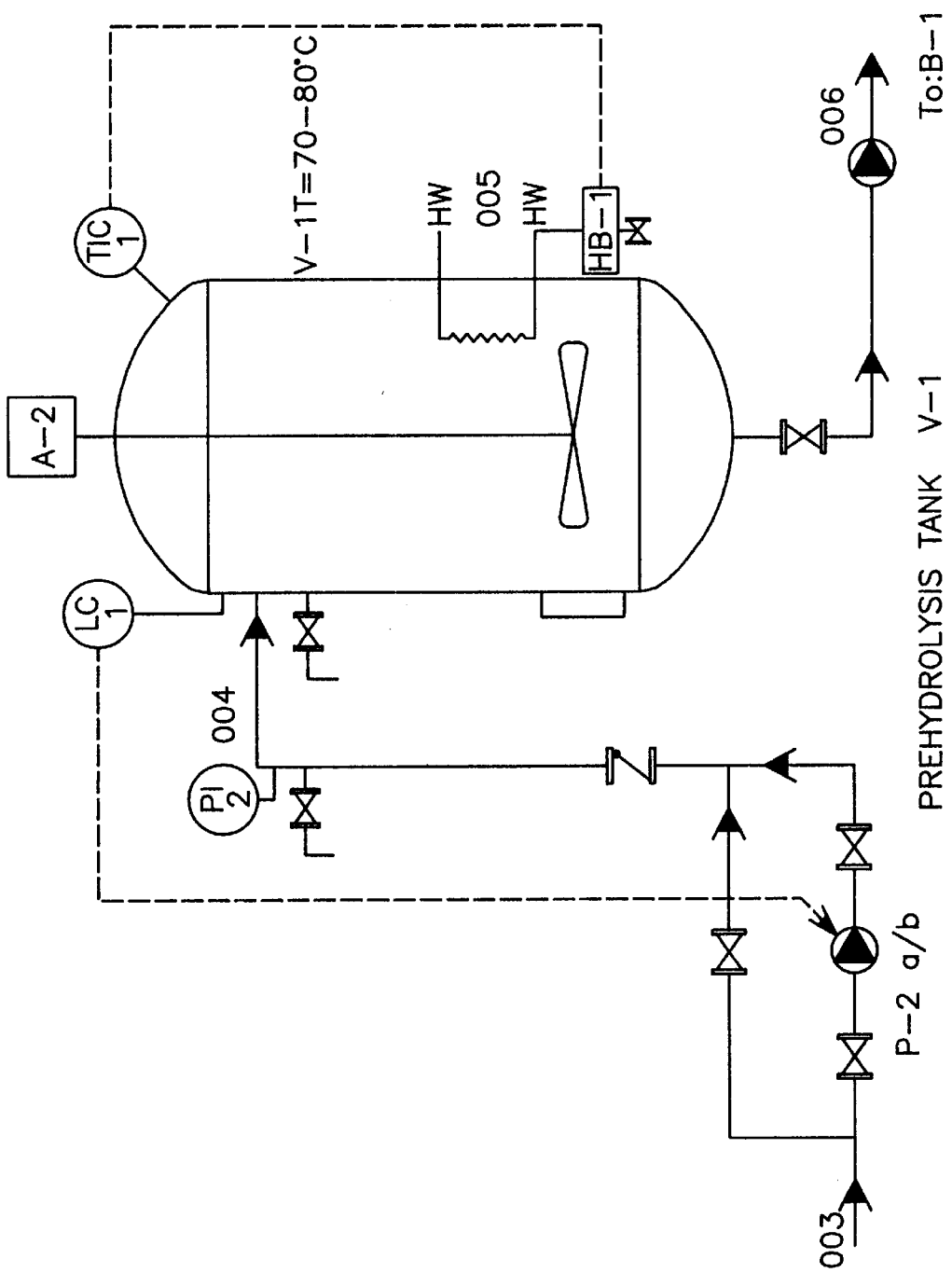
FIG. 5 is a diagram of the prehydrolysis plant.

The process developed consists of:
1. A water floatation unit in which, after cutting the garbage to 3–5 cm, are separated: a) floated products: polymers, used paper and woody materials b) a precipitating part which contains heavy ingredients: metals, glass and inerts, processed to recycle and c) a digestible organic mass which is flowing suspended in water. (FIGS. 1–3)
2. The suspended organic mass after being specially treated to tolerate high presence of lignocellulosics is used to produce energy by anaerobic digestion. (FIG. 5)
3. An aerobic composting unit in which the digested sludge from the anaerobic treatment is processed aerobically to produce mixed fertilizers of humic-chemical-organic composition of high utility and value. (FIG. 4)

Garbage is a mixture of wastes resulting from household everyday life and, to a minor extent, from social and industrial activities. They constitute a mixture containing high values but also contain toxic metals and toxic matter. For the utilization of the garbage there is still research in progress to find solutions which could lead to ecologically balanced complete utilization of the huge existing volumes. However, the knowledge today to come to this achievement is not satisfactory.

The following methods are currently in use:
1. Land-filling is where the garbage is covered with soil to be fermented. If moisture would be available, a part up to 30–35% would have been fermented because the rest is not digestible and accumulates. Land-filling, thus, is an amassment which leads to the creation of nuisances and of hazards in the region, where they operate because of which a strongly negative public opinion has developed.
2. Destruction methods of garbage.

Burning of garbage with addition of oil or of coal which, however, is leading to high investment and operational costs and to emission of toxins in the air and to the disposal of toxic metals in the soil.

Pyrolytic treatment has been developed and worked in practice, by which the garbage are heated up to 500–600° C. in the absence of air to produce gas, a pyrolytic organic mass and activated carbon.

Complete gasification of garbage is advanced in the presence excess of hydrogen at temperatures exceeding the 1000–1100° C. leading to fuel gases of high thermal value. These solutions lead also to intensive investment and to products difficult to market.
3. Fermentation treatments has been advanced for the organic mass.

The composting has been received with enthusiasm, nevertheless, composting with recycling in dry form are procedures of high cost and the compost produced still contains toxic metals and is of low fertility to be accepted.

To realize a useful solution for garbage, their constitution should be considered. In dry form the garbage contains:

| | |
|---|---|
| Paper | 30–35% |
| Food wastes | 30–35% |
| Garden wastes | 5–10% |
| Polymers | 10–12% |
| Metals | 7–8% |
| Glass | 8–9% |

Recycling the garbage together with production of energy by anaerobic digestion would be a solution. In the garbage both recycling and production of energy by anaerobic digestion had to consider the high presence of lignocellulosics. Paper is a 100% such product, the garden wastes are of similar constitution and the food wastes also contain at least 40–50% lignocellulosics. In the whole of digestible mass in garbage, the lignocellulosics make 50 to 60%. There being these problems, and having knowledge of lignocellulosics behaviour in anaerobic digestion in the thermophilic region, which is the other essential item to profitably utilize garbage, we have researched and constructed an original model solution for the profitable utilization of garbage.

The procedure we have invented and considered, runs as follows:

a. The handling of paper in garbage is organized for separation in the incoming mass. We separate paper in amounts making the 70–85% of total paper in garbage.

The written paper is subjected to effective de-inking and then to chemical pulping, wasting about the 30% of the whole. The de-inking is advanced by three successive floating treatments so, at the end a pulp of high brightness is obtained. The pulping to chemical pulp is performed in mild conditions to produce a pulp of high performance. The processing of wastepaper to produce products of value like those described can be advanced only in the facilities offered in the solution we consider. As a result, paper is very effectively and beneficially recycled.

The used paper is taken with the garbage in the flotation line and is mainly collected in the floating part with polymers and woody mass. These are pulped in 4% lime at 90–100° C. after which the mass obtained is screened to effective separation of the polymers to market quality, and a pulp solution is formed which is directed into the hydrolysis tank of the anaerobic digestion unit.

b. The precipitating mass in water flotation consisting of metals, glass, and inerts is collected and separated to products. After being washed, it is subjected to magnetic separation by which 50–60% of the iron metals are collected. The rest is pulverized and subjected once more to magnetic separation after which the iron metals are wholly collected and the remaining mass is heated to 500–600° C. where the soft metals coagulate. That mass is poured into water to most effectively separate the glass and the metals in pure form.

c. The organic mass suspended in water is further pulped to fine constitution and then is subjected to density classification by which are formed three zones: an upper zone of mostly paper and a precipitating zone of heavy articles which are collected and rejected. The main middle part is directed to the anaerobic digestion unit and the upper zone to the co-composting treatment of the digested sludge.

d. The anaerobic digestion unit works in the thermophilic region described in our patent EP. 0474895. The digestible part is subjected to a hydrolysis treatment as a precondition for effective anaerobic digestion. The solution is kept alkaline at pH 9.5–10.5 lime and in that treatment the alkaline wastes in the processing of paper are advanced. The organic mass is kept for 12 hrs. at temperature 80–90° C. maintained by injection raw steam with agitation, after which the mass is pulped and becomes highly digestible. That treatment is essential for effective anaerobic digestion since the organic mass in garbage, because of lignocellulosics present, is not highly biodegradable. Without the pre-hydrolysis treatment the bioconversion is only 50–55% while after the described pre-hydrolysis treatment it reaches highly optimised levels of 80–85%.

e. The wastewater resulting from the anaerobic digestion is purified and recycled. Air stripping is adopted to collect ammonia and decanting for separation of the suspended mass. The wastewater then is subjected to ion exchange treatment in special, ion exchange resins which swell in water up to 300 times and, after these purification treatments, the water is recycled in pure form.

f. Heavy metals, therefore, are not accumulated and the digested sludge received is subjected to co-composting by aerobic fermentation in the thermophilic region at 60–62° C. after which the organic toxicity is also destroyed. Finally fertilizers are obtained of composition: humic 25–30%, chemical 30–35%, organic 35–45%.

The process described for industrial utilization of garbage which is analyzed in the Examples and also shown in the diagrams submitted is original and most profitable, leading to ecologically balanced utilization of garbage.

EXAMPLE 1

In a Pilot Plant which we operated according to our invention, comprising:

a. mechanical means and manual facilities for separating the written papers
b. cutting machine to cut garbage to 3–5 cm length
c. flotation unit to separate recyclables and digestibles
d. unit of anaerobic digestion in the thermophilic region
e. unit of co-composting the resulted digested sludge Garbage 2.5 tons/day of moisture were introduced and of composition: recyclables (paper, polymers, metals, glass, inerts)30–35% and digestibles 65–70%.

The garbage in dry mass had the analysis:

| | |
|---|---|
| recycled paper (separated) | 20–25% |
| used paper | 10–15% |
| polymers | 6–8% |
| metals | 7–8% |
| glass | 5–6% |
| food wastes | 25–40% |
| inerts | 5–10% | a. The Water Flotation Unit

The garbage in quantities 100–120 kg/hr are charged to a cutting machine of 5 HP where they are cut to 2–5 cm and are added to a canal of water of dimensions: 1 m width, 20 m length and 1.5 m depth, of flow 200 m$^3$/hr. The garbage, cut to pieces, is separated during the flow in floating the precipitating part and in suspension in the water digestible part. At the start of the canal a screen is adjusted to recycle the heavier mass to the cutting machine. With the water floating are separated 15–25% of light recyclables, which contain polymers, paper and woody materials, 25–30% of heavy precipitating articles which contain metals, glass and inerts and 45–50% of suspended in the flowing water organic mass. The floating and the precipitation products are continuously withdrawn. The floating products are directed to a tank of 10 m$^3$ where they are washed and the precipitating part are taken in a 5 m$^3$ tank where they are washed and all are processed to trade products. The suspended mass of digestibles of composition: food wastes 70–75%, used paper 10–15% and others 10–15% flows toward the canal end where with a screen, are separated and the water is recycled to the beginning of the canal. The organic mass is then directed to a pulping machine where is pulped to fines to 0.5 mm end is directed to a density classification tank, an upper layer is formed containing polymers and paper (6–8% of dry weight) a precipitating zone is formed consisting of glass metals and inerts (4–7% by weight) and a main mass as central layer consisting of organic digestible matter (45–55% in dry form) which makes a water suspension 10–12% in solids.

With the water flotation treatment the garbage is separated to the following products:

paper 28–35%, recycled by 60–70% polymers 6–8%, recycled by 97–99% metals 6–7%, recycled by 97–98% glass 5–6%, recycled by 99–100% organic digestible part 45–55% dry weight which after the density classification has the composition:

food wastes 80–85% dry weight pulped used paper 10–15% others 1–1.5% b. The Pre-hydrolysis and the Anaerobic Digestion of the Organic Digestible Mass The organic mass as a suspension with 10–12% organic solids in quantity 30–40 kg/hr is charged to the pre-hydrolysis tank. This is a tank of 20 m$^3$ capacity which is heated and agitated with raw steam to 80–90° C. In that tank are directed the alkaline wastes from the anaerobic-digestion and the alkaline wastes from the paper processing and the tank solution with addition of lime is kept at 9.0–10.0 pH and with solid content of 5–8%. In those conditions the organic mass consisting mainly of lignocellulosics, is partly hydrolyzed in a physical-chemical biological treatment with very beneficial results for the anaerobic digestion. This quantity, with flow 5–6% in organic solids, is directed to the bioreactor of slurry bed type and are advanced all the biological reactions that of hydrolysis, that of acidogenesis, that of ecetogenesis leading to methanogenesis in a surrounding of high biological activity with increased presence of bicarbonates (150 gr/lt) in which are based beneficial operations of bioreactions and is inhibited the production of hydrogen sulfide from the biotransformation of sulfur containing organic and inorganic substances. All these benefits of operation and others are described in our patent EP. 0474895.

c. The Waste Water Handling

On the line of wastewater resulting after the anaerobic digestion a unit of ammonia stripping is installed comprising of a pipe type perpendicularly placed tank of 10 m$^3$ capacity filled with solid material of high specific surface (140 m$^2$/m$^3$). The wastewater feeding is from top with steam while reversibly air is introduced. The water is collected in the tank bottom and is further treated to be recycled. The air coming through is rich in ammonia and is directed to the co-composting unit for the digested sludge with flow 1.000 m$^3$/m$^3$ of wastewater treated. The wastewater after precipitation or decanting treatment is introduced to a tank where an anodized steel frame is hanged containing ion exchange resins of the special type described which swell in water 150–250 times and make a product easily introduced and removed. The potential of the ionexchange resins is high and the column can collect 500 gram equivalent of heavy metal ions. That ion exchange treatment collects all metal ions and the water becomes soft and free of metal toxicity and thus is recycled.

d. The Digested Sludge Utilization

The sludge resulted from the anaerobic digestion containing 17–20% solids is charged to a substrate consisting of density classification floating matter which with aeration is advanced at a thermophilic compost treatment at 58–62° C. At that temperature the addition of sludge starts at a rate so that temperature is kept at 58–82° C. because of highly exothermic fermentation which is controlled by water evaporation. At the end, a humic mass is formed accumulated for 40 days which is taken out and stored in heaps for ripening and mixing and at the end results in a product composition: humic 35%, chemical fertilisers 30%, organic mass 35% which is a fertiliser of high utility and of value.

EXAMPLE 2

The products to separate after water flotation treatment are:

i. the heavy products which sink (metals, glass, inerts) and ii. the light products which float (polymers, used paper, woody mass) which are in high proportion of the garbage dry weight and their utilization to commercial products is necessary.

The heavy products received 10–30% dry weight are washed and subjected to magnetic separation and the 50% of iron metals are collected. After it the mass is pulverised finely to 1–3 mm and is subjected to a second magnetic separation and the iron metals are all collected. The remaining mass is heated to 500–600° C. where the soft metals coagulate and are separated from the glass received all in high purity and waste mass after dumping in water.

Per ton of heavy articles are received:

| | |
|---|---|
| iron metals | 308–320 kg |
| soft metals | 9–12 kg |
| glass | 260–320 kg |
| soil wastes | 250–320 kg |

The floated matter which contains polymers, used paper and woody mass (15–20% by dry weight) is subjected to pulping with boiling for two hrs. in presence of 4% lime. The mass is screened to collect the polymers in pure form of market quality and the pulped paper and woody mass is screened and directed to the anaerobic digestion to produce energy or is collected for industrial use.

EXAMPLE 3

Written paper mechanically or manually collected from the garbage is treated to produce de-inked pulp and chemical quality pulp. 20 kg of written paper is cut to 5–6 cm and subjected to chemical de-inking treatment in a water solution containing 3.0 kg lime, 1% hydrogen peroxide and 3% silicium oxide in volume 1:6. It is agitated strongly at 50° C. for 2 hrs. and then is screened and the wastewater resulted is taken in the wastewater line.

Then it is directed into floating units three in series containing 0.6% of sodium oleate and 0.1% silicium oxide with solids to water ratio of 1:10. It is aerated to foaming and the foams formed are taking the ink colored matter. This treatment in three floatations leads to a product pulp of analysis:

| Chemical analysis | | Technical analysis | |
|---|---|---|---|
| cellulose | 50–60% | breaking length | 3.3 km |
| hemicellulose | 20–25% | tearing factor | 5.9 |
| lignin | 15–20% | yield | 89% |
| ash | 5–10% | brightness | 71 |

This quality pulp is already a commercial product. However, it is further treated to produce chemical quality pulp. For this it is subjected to mild pulping conditions:

a. pulping with chlorine b. pulping with oxygen c. pulping with air

A. Chlorine Pulping

In the initial pulp 5 kg taken in 10 lt. of water is introduced chlorine gas 5 lt./hr-kg of pulp under stirring at 30° C. The chlorination proceeds to color change which becomes purple. The colour tone determines the reaction proceedings and when the chorine introduction terminates nitrogen is introduced to expel the unreacted chlorine. The product is poured into a 3% sodium hydroxide solution to neutralize it and to extract the chlorinated lignin.

The pulp is received in high color quality and of very low lignin, lower than 4% and shows the following technological characteristics:

| | |
|---|---|
| breaking length | 10.000 m |
| folding efficiency | 800 |
| tearing strength | 15.6 |
| color | 80 lovipont units |
| 25% chlorinated lignin is also produced | |

B. Oxygen Pulping 5 kg. initial pulp is taken in 10 volumes of water containing 16% of NaOH and 1% $MgCO_3$ to the weight of the pulp. The whole is heated to 120° C. for 60 minutes in the presence of oxygen of pressure 2 atm. and of flow 5 lt/kg pulp-hr.

The pulp material is washed with water and received in yields 69% with the following technological parameters:

| | |
|---|---|
| breaking length | 9.000 m |
| folding efficiency | 900 |
| tearing strength | 10.8 |
| color | 79 lovipont units |
| lignin at a yield of 15.2% was also received | |

C. Pulping with Air

Using of air in the conditions of B. by introducing air 20 lt./kg pulp-hr a pulp in yield 70% is received with the following characteristics:

| | |
|---|---|
| breaking length | 8,200 m |
| folding efficiency | 800 |
| tearing strength | 8.8 |
| color | 78 lovipont units |
| lignin was also received at a yield of 14.8% | |

That way the paper is received in two qualities of pulp in de-inking pulp and in chemical pulp both of which are of high market values. The production is advanced within the garbage industrial unit for profitably utilizing the wastewater formed.

What is claimed is:

1. A method for recycling and utilizing garbage which comprises:

separating printed paper;

cutting the garbage to about 3–5 cm pieces;

subjecting the garbage to water canal floatation;

collecting light floating products;

precipitating heavy products;

cleaning organic mass suspended in the water;

hydrolyzing the organic mass at a pH range of about 9.5–10 at a temperature range from about 80–100° C.;

subjecting the organic mass to anaerobic digestion in a thermophilic region to produce biogas and sludge; collecting the sludge; and subjecting the sludge to aerobic co-composting at a temperature of about 60° C. to produce humic-chemical-organic mixed fertilizers.

2. The method according to claim 1, wherein the light floating products are at least one selected from the group consisting of paper, polymers and woody mass.

3. The method according to claim 1, wherein the heavy products are at least one selected from the group consisting of metal, glass and inerts.

4. The method according to claim 1, further comprising:

processing the separated printed paper to produce de-inked pulp or chemical pulp.

5. The method according to claim 1, further comprising:

pulping the light floating products with about 4% lime at a temperature range of about 80–100° C. to pulp cellulosics; and separating polymers by screening.

6. The method according to claim 1, further comprising:

subjecting the precipitated products to magnetic separation to collect iron metal;

pulverizing the iron metal;

subjecting the pulverized iron metal to magnetic separation to collect all the iron metal;

heating a non-iron metal part of the precipitated products at a temperature of about 600° C. to coagulate soft metals; and introducing water to separate the coagulated soft metals from glass.

7. The method according to claim 1, further comprising a pre-hydrolyzing step of treating the garbage with alkaline wastewater from paper pulping, whereby the bioconversion of lignocelluosics is improved.

8. The method according to claim 7, wherein the pre-hydrolysis step uses lime as an alkaline reagent and a retention time is in a range of about 10 to 12 hours.

9. The method according to claim 1, wherein the anaerobic digestion produces wastewater, and the wastewater is processed using the steps of:

air-stripping to collect ammonia;

decanting to collect suspended matter; and ion-exchanging in special resins which swell up to 300 times in water, whereby the wastewater becomes entirely free from toxic metals.

10. The method according to claim 9, wherein the aerobic co-composting step further comprises aerating the sludge with ammonia containing air from the air-stripping step.

11. The method according to claim 1, wherein the biogas is used to produce electric energy.

12. The method according to claim 11, wherein the electric energy is produced in combined cycle installations, whereby the garbage is utilized to give high values and nothing is rejected.

13. The method according to claim 1, wherein the biogas has high fuel value.

14. A method for recycling and utilizing garbage which comprises:

floating the garbage in water;

hydrolyzing a suspended organic mass; and digesting the organic mass anaerobically to produce biogas and sludge.

15. The method according to claim 14, which further comprises:

subjecting the sludge to aerobic co-composting.

16. The method according to claim 14, wherein the biogas is used to produce electricity.

17. The method according to claim 14, which further comprises:

separating printed paper prior to floating the garbage.

18. The method according to claim 14, which further comprises:
  collecting light floating products after floating the garbage; and
  precipitating heavy products after floating the garbage.

19. The method according to claim 14, wherein the hydrolyzing is performed at a pH of 9.5–10 at a temperature of about 80–100° C.

* * * * *